US008692213B2

(12) United States Patent
Abenaim et al.

(10) Patent No.: US 8,692,213 B2
(45) Date of Patent: Apr. 8, 2014

(54) ACCURATE OPERATIONAL SURFACE HANDLING

(75) Inventors: Daniel Abenaim, Lynnfield, MA (US); Gilbert McKenna, Revere, MA (US)

(73) Assignee: Analogic Corporation, Peabody, MA (US)

( * ) Notice: Subject to any disclaimer, the term of this patent is extended or adjusted under 35 U.S.C. 154(b) by 302 days.

(21) Appl. No.: 12/862,989

(22) Filed: Aug. 25, 2010

(65) Prior Publication Data
US 2012/0049084 A1  Mar. 1, 2012

(51) Int. Cl.
*A61B 6/04* (2006.01)

(52) U.S. Cl.
USPC ............. 250/492.1; 250/453.11; 73/863; 378/4; 378/20; 378/208; 5/601; 5/622; 5/81.1 C; 5/81.1 R; 5/943

(58) Field of Classification Search
USPC ......... 250/453.11, 492.1; 73/863; 378/4, 20, 378/208; 5/601, 622, 81.1 C, 81.1 R, 943
See application file for complete search history.

(56) References Cited

U.S. PATENT DOCUMENTS

| 4,105,923 A * | 8/1978 | Hynes, Jr. ................. 378/20 |
| 4,131,802 A * | 12/1978 | Braden et al. ............. 378/20 |
| 4,671,728 A * | 6/1987 | Clark et al. ............... 414/401 |
| 4,688,278 A * | 8/1987 | Van Aspert ............... 5/601 |
| 4,914,682 A * | 4/1990 | Blumenthal ............... 378/20 |
| 5,034,970 A | 7/1991 | Yahata et al. |
| 5,606,970 A * | 3/1997 | Damadian ................. 600/415 |
| 6,640,364 B1 * | 11/2003 | Josephson et al. ........ 5/601 |
| 6,668,403 B2 * | 12/2003 | Seufert ..................... 5/601 |
| 6,776,527 B1 * | 8/2004 | Tybinkowski et al. .... 378/209 |
| 7,065,813 B2 * | 6/2006 | Hoth et al. ................ 5/601 |
| 7,120,223 B2 * | 10/2006 | Nafstadius ................ 378/20 |
| 7,360,949 B2 * | 4/2008 | Izuhara et al. ............ 378/209 |
| 7,467,004 B2 * | 12/2008 | Calderon et al. .......... 600/415 |
| 7,784,121 B2 * | 8/2010 | Ahlman .................... 5/81.1 R |
| 7,810,187 B2 * | 10/2010 | Van Es et al. ............. 5/601 |
| 8,166,586 B2 * | 5/2012 | Bridge et al. .............. 5/601 |

(Continued)

FOREIGN PATENT DOCUMENTS

DE      4340358 A1 *  6/1994  ............ A61G 3/00
GB      2092077 A  *  8/1982  ............ A61G 1/003

OTHER PUBLICATIONS

"Computed Tomography Imaging"; http://belley.org/ct/ct/; Retrieved on: Jul. 20, 2010.

(Continued)

*Primary Examiner* — Michael Logie
(74) *Attorney, Agent, or Firm* — Cooper Legal Group LLC

(57) ABSTRACT

One or more techniques and/or systems are described herein for handling an examination surface for radiology or other operations. That is, an examination surface support structure can be integrally coupled with a support component of a radiology apparatus so that an examination surface and an object optionally placed thereon are supported during an operation. An examination surface transport component can be docked with an examination surface docking component that is operably coupled with the examination surface support structure so that the examination surface can be exchanged between the transport component and the radiology apparatus. An examination surface transit component that is operably coupled with the examination surface support structure can engage the examination surface in order to move the examination surface into and out of an operation region of the apparatus, such as during a scanning or dosage operation.

20 Claims, 12 Drawing Sheets

(56) References Cited

U.S. PATENT DOCUMENTS

| | | | |
|---|---|---|---|
| 2001/0054851 A1* | 12/2001 | Tsuboi et al. | 310/12 |
| 2002/0104163 A1* | 8/2002 | Reimann | 5/601 |
| 2004/0057557 A1* | 3/2004 | Nafstadius | 378/209 |
| 2005/0034237 A1* | 2/2005 | Lenting et al. | 5/600 |
| 2006/0096028 A1* | 5/2006 | Gallant et al. | 5/81.1 R |
| 2006/0167356 A1* | 7/2006 | Everett et al. | 600/407 |
| 2007/0039101 A1* | 2/2007 | Luginbuhl et al. | 5/600 |
| 2007/0133743 A1* | 6/2007 | Johnson et al. | 378/57 |
| 2008/0191696 A1* | 8/2008 | Van Der Burgt | 324/318 |
| 2009/0056023 A1* | 3/2009 | Calderon et al. | 5/601 |
| 2010/0162488 A1* | 7/2010 | Dahlin et al. | 5/600 |
| 2011/0173752 A1* | 7/2011 | Weiler | 5/601 |

OTHER PUBLICATIONS

"System Components"; http://belley.org/ct/ct/objective02/index.htm; Retrieved on: Jul. 20, 2010.

"Patient Table"; http://belley.org/ct/ct/objective04/index.htm; Retrieved on: Jul. 20, 2010.

* cited by examiner

Accurate Operational Surface Handling

BACKGROUND

The present application relates to surface handling. It may find particular application to medical, security, and/or other applications where an object is placed on a surface and subjected to an operation using a device.

By way of example, radiographic imaging or therapy systems, such as computed tomography (CT), nuclear medicine, positron emission tomography (PET), single photon emission computed tomography (SPECT or SPET) magnetic resonance imaging (MRI), line scanners, combination(s) thereof such as PET-CT or SPECT-CT, radiotherapy systems etc., provide information, or images, of an object under examination (e.g., interior aspects of an object under examination), and/or treat aspects or regions of an object. In some systems, the object is exposed to radiation (e.g., x-rays, gamma rays,) or emits radiation (positron emissions), and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or gun, for example, will be apparent when surrounded by less dense objects, such as fatty tissue or clothing, for example. A detector array, generally positioned opposite a radiation source from which radiation is emitted relative the object under examination, is configured to detect radiation that traverses the object under examination and convert such radiation into signals and/or data that may be processed to produce the image(s). Such an image(s) may be viewed by security personnel to detect threat items (e.g., weapons, etc.) and/or viewed by medical personnel to detect medical conditions (e.g., cancerous tissue).

In some scanners, such as three-dimensional imaging scanners (e.g., CT scanners, etc.), for example, the detector array and radiation source are mounted on opposing sides of a rotating gantry that forms a ring, or donut, around the object under examination. In such a scanner, the rotating gantry (including the radiation source and/or detector array) is rotated in a circle situated within an x, y plane about a z axis substantially perpendicular to the x, y plane (e.g., an "isocenter") during an examination. The object is generally supported by a support article (e.g., a bed, conveyor belt, etc.) that runs in the z direction substantially parallel to the mechanical center of rotation (e.g., the isocenter). As the rotating gantry is rotated, radiation is substantially continuously emitted from a focal spot of the radiation source toward the object under examination.

Commonly, in one or more of the aforementioned or other systems, the examination table (e.g., where the object/patient lies during a scan or other operation) is a separate assembly that comprises its own supports attached to the floor, and the scanning or other apparatus comprises its own supports that are attached to the floor. In radiotherapy or radiation therapy, for example, where (photon) radiation is used for treatment (e.g., of cancer), a separate assembly is used for manipulating the operational surface so that that the patient is appropriately treated with a dose of radiation.

In such systems, the examination table comprises mechanical components that provide support for the patient being moved to the operational region (e.g., scan plane or dosage plane). The examination table, as a separate assembly, can be properly aligned with and coupled with a scanner or radiation dosage device so that when the patient is moved into the examination or dosage region they are in the appropriate focal plane for scanning or dosage. Currently, there are at least two reasons for having a separate examination table assembly, at least with regard to a scanning apparatus: first, providing a separate table allows the gantry to tilt the scan plane with respect to the patient; second, the separate table assembly allows independent vertical motion of the table to ease patient loading and placement in the bore of the rotating gantry.

However, these reasons for having a separate table assembly have inherent problems. The examination table must be able to cantilever the patient through the bore without appreciable motion (e.g., vibration), while also providing vertical and horizontal motions with a high degree of accuracy over a long distance. Therefore, the table needs to be properly aligned, and the (rigid) cantilevered design with accurate movements adds cost to the examination table. Moreover a separate examination table utilizes its own stable frame and skins that can also add cost, and the structure must also be firmly docked to the gantry which can prevent pre-scanning operations (e.g., patient prep.) from being performed on the target object at a location remote from the scanner.

SUMMARY

Aspects of the present application address the above matters, and others. According to one aspect, an apparatus for handling an examination surface is provided. The apparatus comprises an examination surface support structure that is integrated with a support component of an apparatus, and the examination surface support structure is configured to support an examination surface and an object optionally situated on the examination surface. The apparatus further comprises an examination surface docking component that is operably coupled with the examination surface support structure, and the examination surface docking component is configured to dock with an examination surface transport component in order to exchange the examination surface between the transport component and the apparatus. Additionally, the apparatus comprises an examination surface transit component that is operably coupled with the examination surface support structure, and configured to move the examination surface into and out of an operation region of the apparatus.

According to another aspect, a method for handling an examination surface having an object optionally situated thereon for examination with an apparatus is provided. The method comprises interfacing a transport carrying the examination surface, with the object optionally placed thereon, with an examination surface dock on the apparatus. Further, the method provides that the examination surface is exchanged between the transport and the examination surface dock. Additionally, the method provides for the examination surface engaging with an examination surface transit so that the examination surface can be moved into and out of an examination region of the apparatus.

According to yet another aspect, a radiographic scanning system is provided. The radiographic scanning system comprises a rotating gantry portion, and a non-rotating portion that is operably associated with the rotating portion in order to facilitate an examination of an object. The radiographic scanning system further comprises a support structure that is operably associated with the non-rotating portion and it is configured to selectively receive one or more examination surfaces so that object(s) optionally placed upon the examination surface(s) may be examined. The support structure is configured to articulate an examination surface and object thereon, relative to the non-rotating portion.

FIGURES

The application is illustrated by way of example and not limitation in the figures of the accompanying drawings, in which like references indicate similar elements and in which.

Figure 6A:
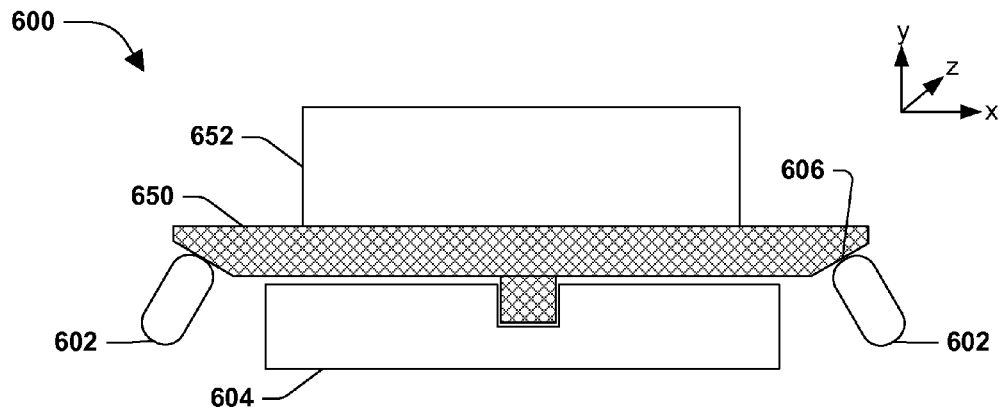
Figure 6B:
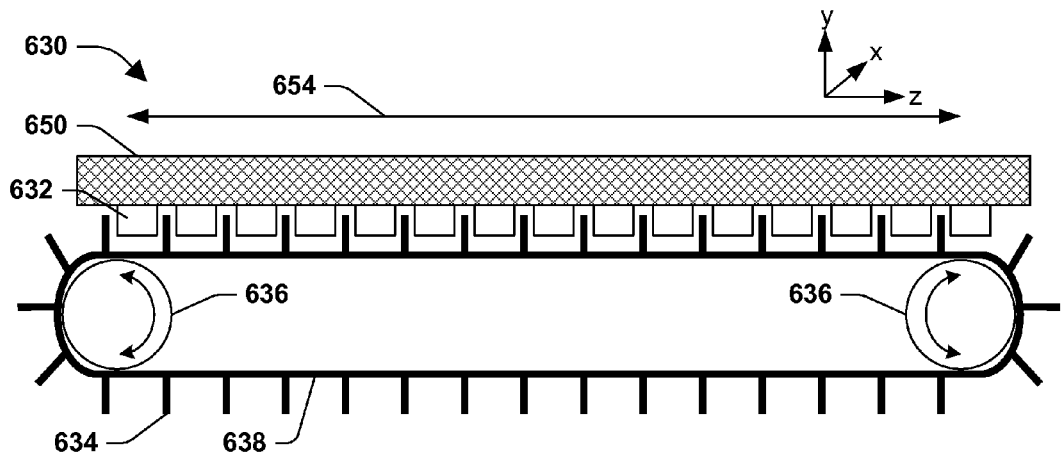
Figure 6C:
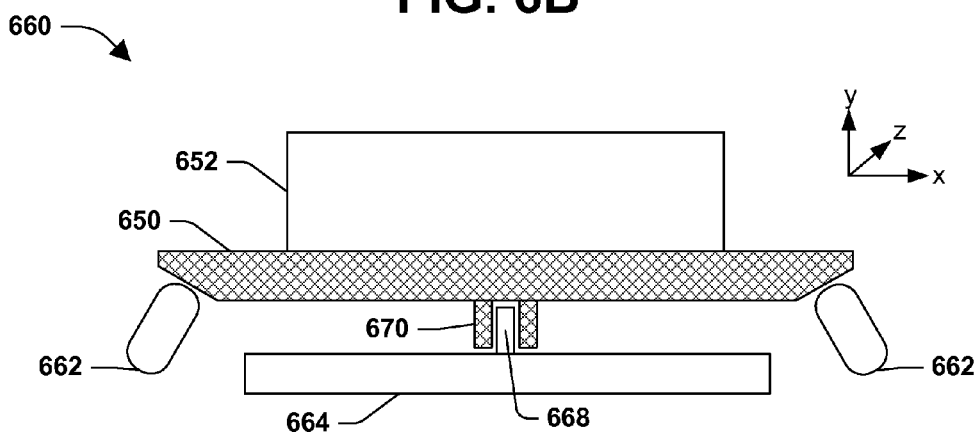

FIGS. 6A-C are are component diagrams illustrating example embodiments of one or more portions of an apparatus described herein.

Figure 7:
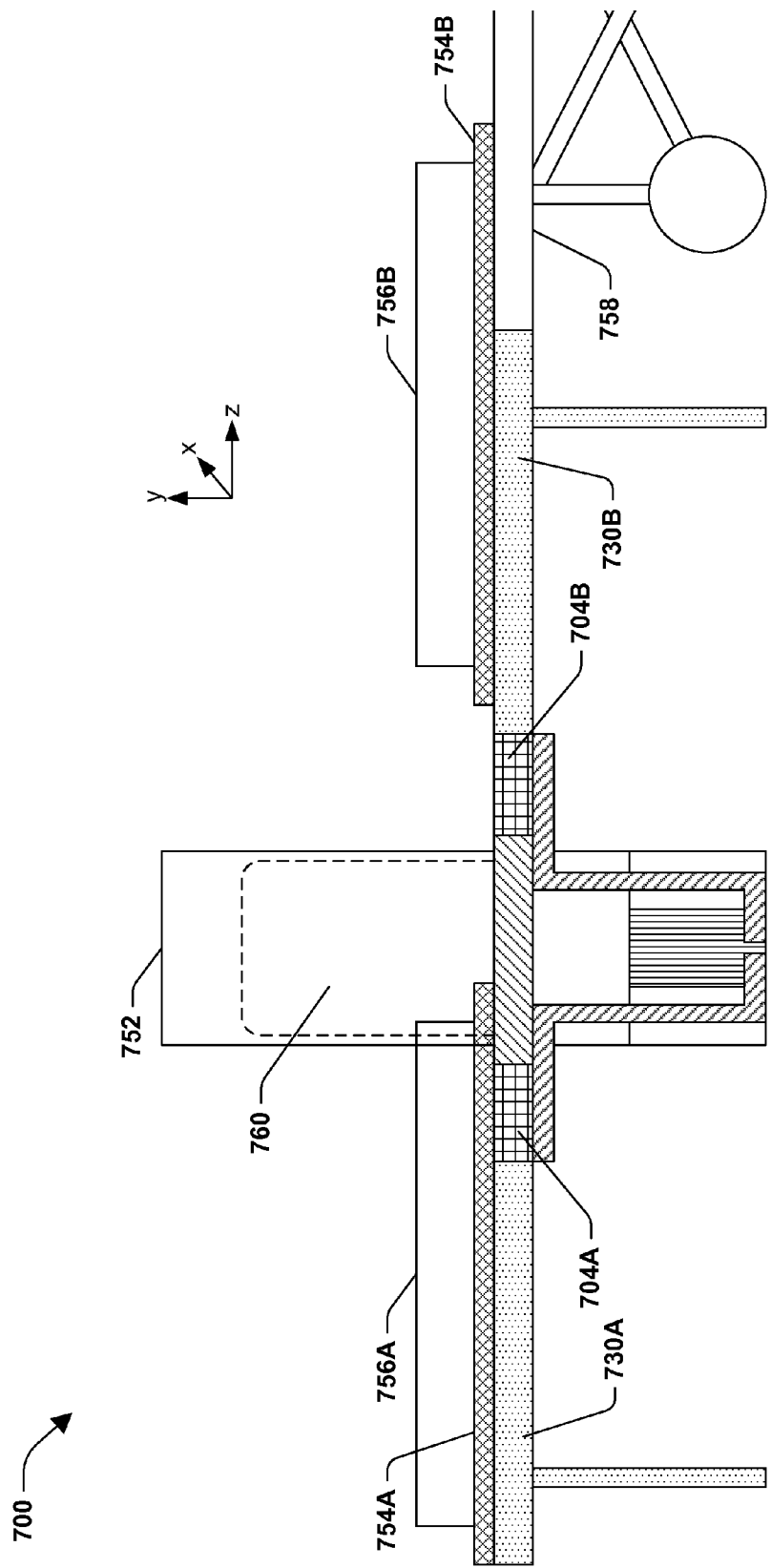

FIG. 7 is a component diagram illustrating an example embodiment of one or more portions of an apparatus described herein.

Figure 8:
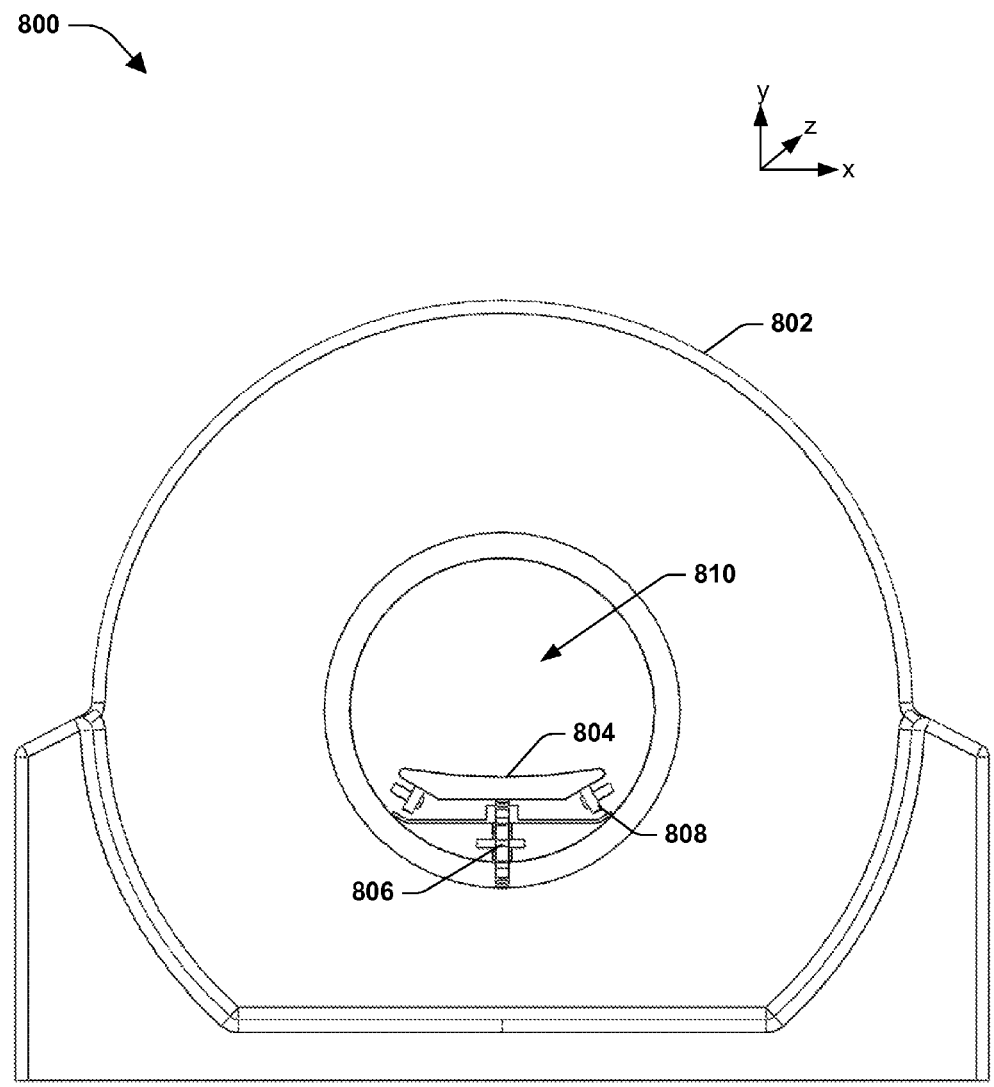

FIG. 8 is a component diagram illustrating an example embodiment of one or more portions of an apparatus described herein.

Figure 9:
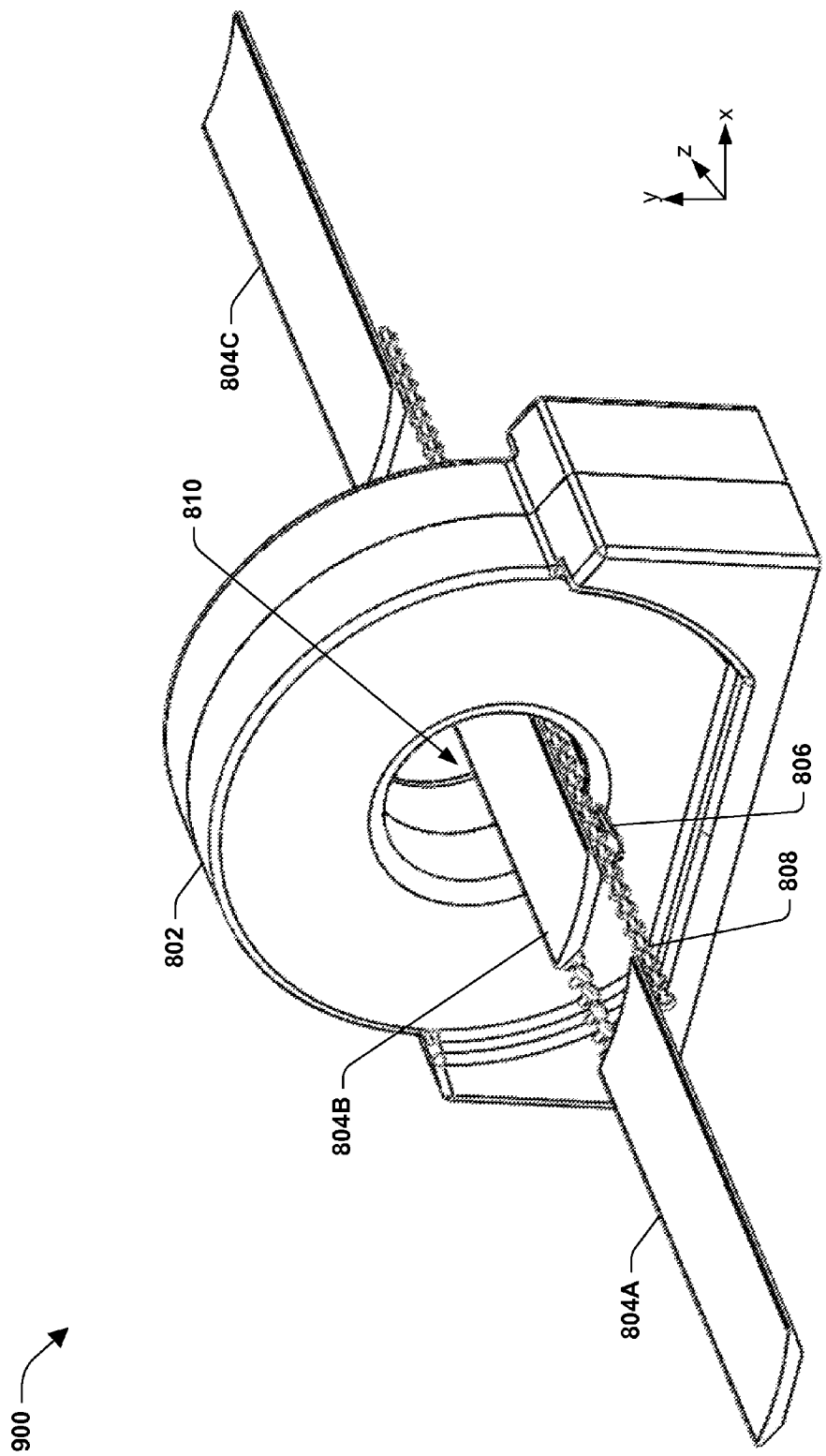

FIG. 9 is a component diagram illustrating an example embodiment of one or more portions of an apparatus described herein.

Figure 10:
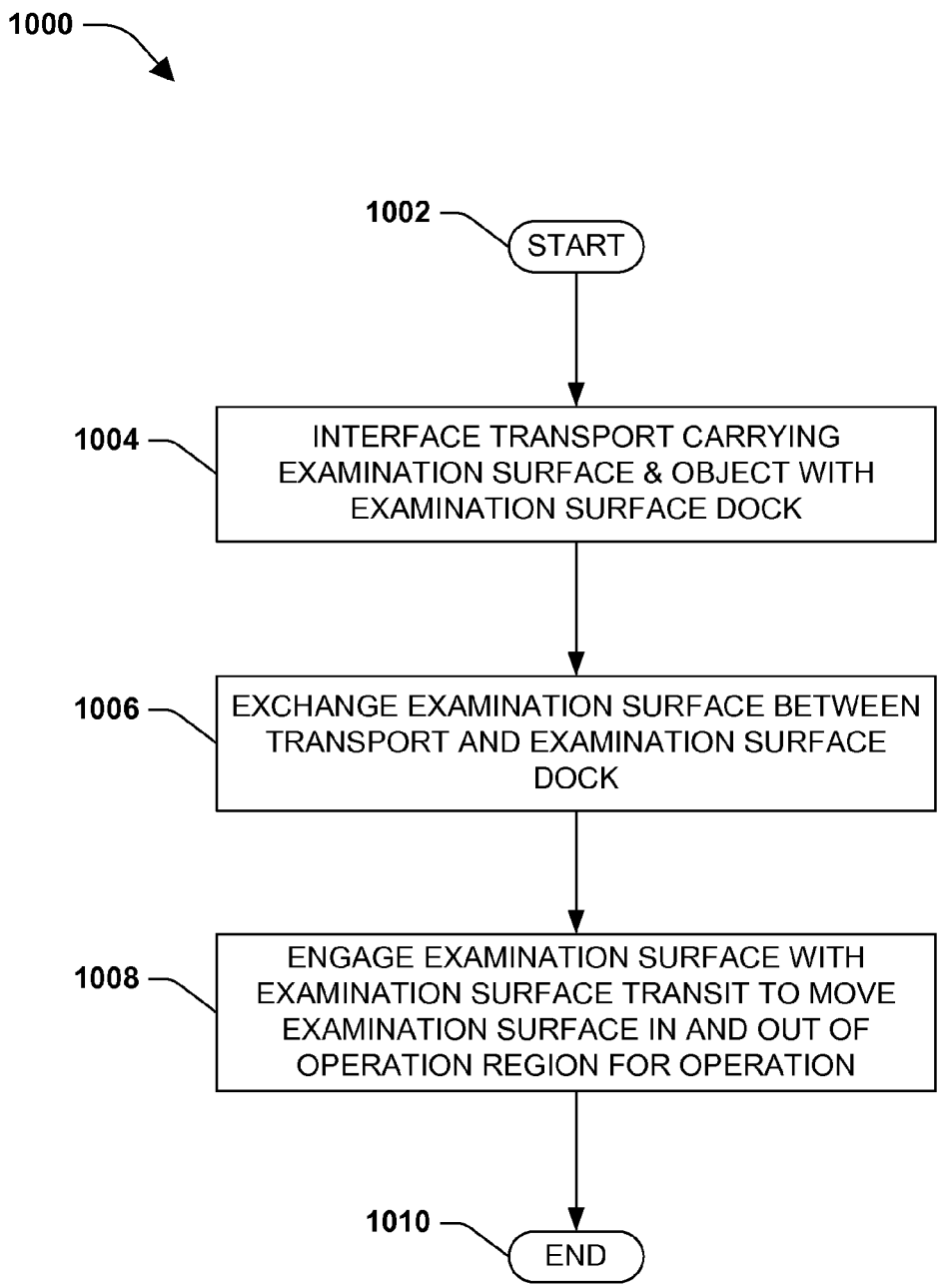

FIG. 10 is a flow diagram illustrating an example method for handling an examination surface.

Figure 11:
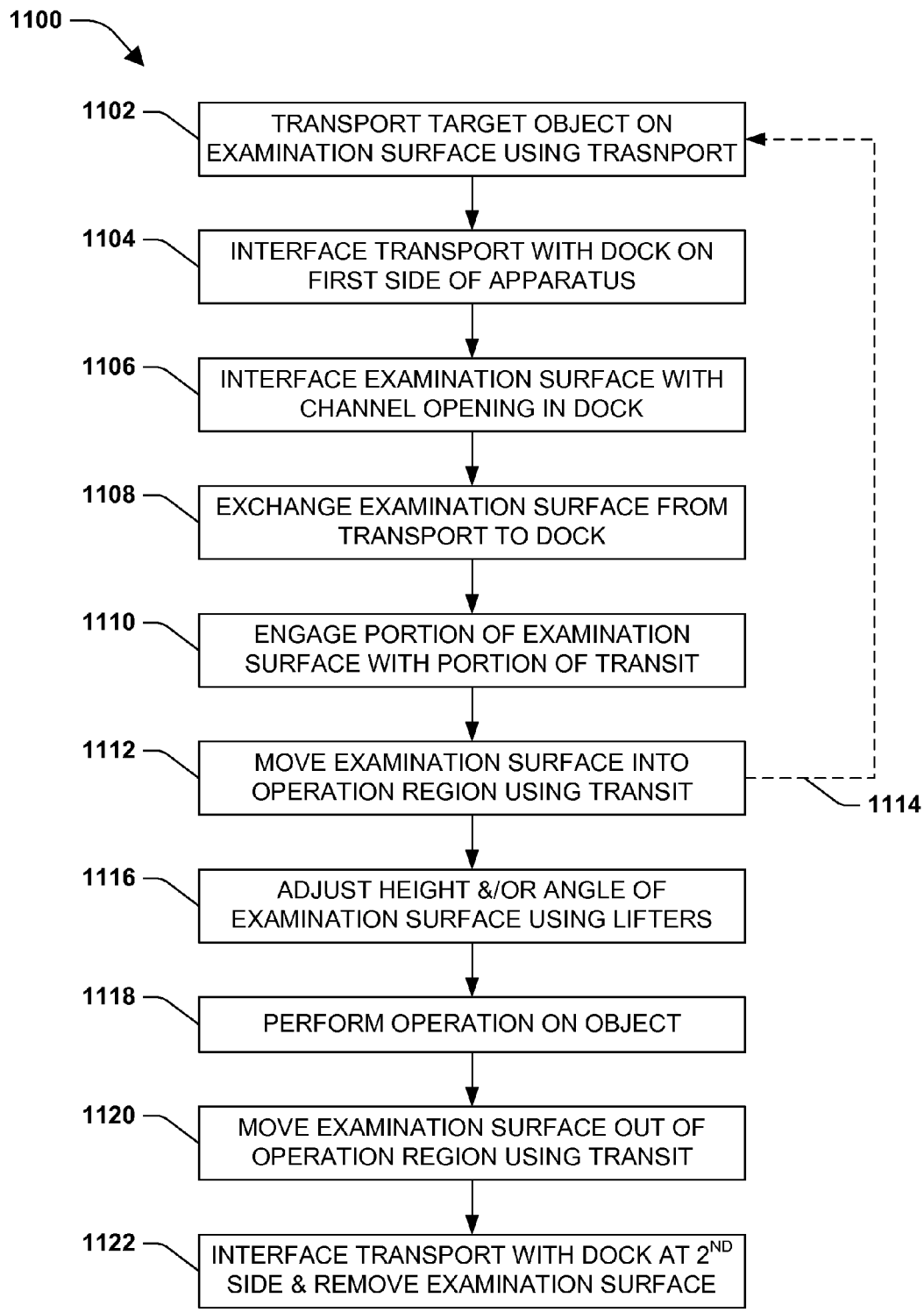

FIG. 11 is a flow diagram illustrating an example embodiment of one or more portions of a method described herein.

DESCRIPTION

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more techniques and/or systems for handling an examination surface are provided herein, which may provide several significant advantages. Some advantages may include, but are not limited to, lower cost, smaller size/footprint, higher throughput of target objects, easier object (e.g., patient) loading, and easier fusion of images from different modalities, for example. It will be appreciated that while some of the discussion herein pertains to imaging or scanning systems (e.g., CT), for example, that the application and/or claimed subject matter are not intended to be so limited. Instead, the application and claimed subject matter are intended to cover other situations as well. That is, an imaging or scanning application is merely one context where accurate operational examination surface handling may be implemented as provided herein. By way of example, and not limitation, accurate examination surface handling may likewise be implemented in the context of (photon) therapy systems, or combination systems fusing information from more than a single modality, for example. Accordingly, where terms such as x-ray, radiation, radiology, radiographic, radiography, radiotherapy, scan, scanning, etc. are used herein in association with and/or to identify or define a system, apparatus, device, etc., the application and/or claimed subject matter are not intended to be limited thereby (e.g., limited to the example radiographic system, apparatus, device, etc.). Similarly, terms such as "examination" and "operation" and variations thereof as used herein are generally intended to be interchangeable. For example, an object, patient, etc. can be said to be on an examination, operation, operational, etc. surface such that the objet, patient, etc. (or portion thereof) may undergo an exam, an examination, an operation, etc. in an exam, examination, operation, operational, etc. region of an apparatus, for example (e.g., scanned to obtain image data and or treated in some manner). Accordingly, unless specified otherwise, particular use of one or more of such terms is not intended to limit the scope of the application and/or claimed subject matter.

Figure 1A:
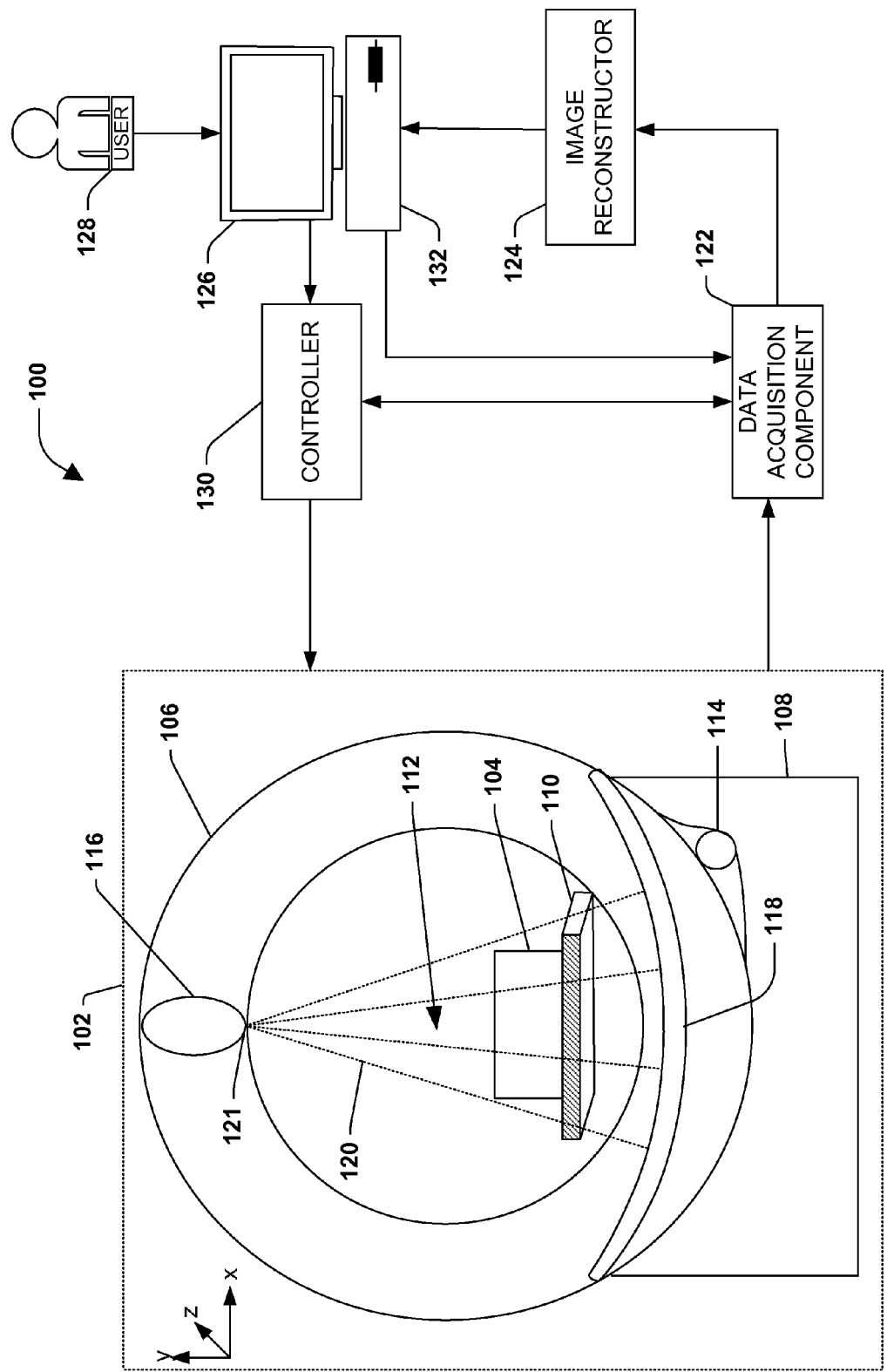
FIG. 1A is a schematic block diagram illustrating an example radiation system.

FIG. 1A is an illustration of an example environment 100 in which data that is generated from components comprised within a rotating gantry 106 of a radiography scanner (e.g., a CT scanner) may be acquired so that one or more images of an object 104 under examination may be produced and displayed on a monitor 126, for example, such as for viewing by a human user 128. Such a scanner may be used to identify a tumor in a human patient at a medical center or in an animal at a veterinary clinic, and/or to identify objects of interest (e.g., potential threat objects, banned objects) associated with (e.g., comprising, comprised within, etc.) an object 104 (e.g., luggage) under examination at a security checkpoint, for example. In another embodiment, no image is generated, but the density of the object can be identified and compared with a list of densities associated with predetermined items (e.g., banned items) to determine if the object 104 potentially comprises one or more of the predetermined items. It will be appreciated that while a CT scanning system is described herein, the instant application is not intended to be so limited. That is, to the extent possible, the instant application, including the scope of the claimed subject matter, is intended to be applicable to other systems as well (e.g., Pet-CT systems, SPECT-CT systems, radio therapy systems, line scanners, etc.).

In the example environment 100, the scanner comprises an object scanning apparatus 102 configured to examine one or more objects 104 (e.g., a series of suitcases at an airport, a human patient, etc.). The object scanning apparatus 102 can comprise a rotating gantry 106 and a stationary gantry 108. During an examination of the object(s) 104, the object(s) 104 can be placed on a support article 110 (e.g., examination surface), such as a bed or conveyor belt, that is selectively positioned in an examination region 112 (e.g., a hollow bore in the rotating gantry portion 106), and the rotating gantry 106 can be rotated about the object(s) 104 by a rotator 114 (e.g., motor, drive shaft, chain, etc.).

The rotating gantry 106 may surround a portion of the examination region 112 and comprises a radiation source 116 (e.g., an ionizing x-ray source) and a detector array 118 that is mounted on a substantially diametrically opposite side of the rotating gantry 106 relative to the radiation source 116 (e.g., where a focal spot 121 of the radiation source 116 would generally serve as a center of the detector array 118 should the detector array completely encircle the radiation source 116).

During an examination of the object(s) 104, the radiation source 116 emits radiation 120 towards the object(s) 104 under examination while the rotating gantry 106 (including the radiation source 116 and detector array 118) rotates about the object(s) 104. Generally, in a CT scanner, the radiation 120 is emitted substantially continuously during the examination. However, in some CT scanners and/or in other radiography scanners, the radiation 120 may be emitted intermittently during the rotation.

As the radiation 120 traverses the object(s) 104 and support article 110, the radiation 120 may be attenuated differently by different aspects of the object(s) 104. Because different aspects attenuate different percentages of the radiation 120, an image may be reconstructed based upon the attenuation, or rather the variations in the number of photons that are detected by the detector array 118. For example, more dense aspects of the object(s) 104, such as a bone or metal plate, may attenuate more of the radiation 120 (e.g., causing fewer photons to strike the detector array 118) than less dense aspects, such as skin or clothing.

In some embodiments, while the object(s) 104 is being scanned, or examined, the object(s) 104 may be translated along an axis traveling in the z-dimension (if, as illustrated, the rotating gantry 106 is configured to rotate in an x, y plane). In this way, an object that has a z-dimension greater than the z-dimension of the radiation traversing the object may be scanned more quickly (relative to a step-and-shoot scanning approach). It will be appreciated that if the object(s) 104 is being translated (e.g., in the z direction) during a scan while the rotating gantry 106 is rotating (e.g., in the x, y plane), the scan may be referred to as a helical or spiral scan.

Radiation 120 that impinges the detector array 118 generally creates an electrical charge that may be detected by one or more pixels, or elements, of the detector array 118 that are in close spatial proximity to the location where the radiation impinged. Respective pixels generate an analog signal (in a linear format) indicative of the electrical charge detected, which is fed to a data acquisition component 122. Because the electrical charge detected by the one or more pixels is directly related to the number of photons (e.g., an electrical charge of 1.2 keV may be equivalent to one photon), the output is indicative of the attenuation of the radiation 120 as it traversed the object(s) 104. It will be appreciated that, in one embodiment, when a pixel is not detecting electrical charge, the pixel can emit an analog, baseline signal that indicates that the pixel has detected little to no electrical charge.

It will be understood to those skilled that in some embodiments, an analog to digital (A/D) signal converter (not shown, but generally operably coupled with or comprised within the detector array 118 and/or the data acquisition component 122) may be configured to receive the analog signals and convert the signals into digital signals, such as by using digital timing comparison of the incoming signal to a known signal. The data acquisition component 122 is configured to prepare the output signals, in projection space, for an image reconstruction component 124. In one embodiment, configuring the output signals for reconstruction can comprise remapping (also referred to herein as converting or encoding) the output signals from a first format to a second format that is more suitable for reconstruction from projection space to image space, for example.

In the example environment 100, signal data from the data acquisition component 122 is transmitted to an image reconstructor 124 configured to receive the projection space data, for example. The image reconstructor 124 is configured to reconstruct one or more images of the object 104 under examination using analytic, iterative, or other image reconstruction techniques known to those skilled in the art (e.g., 2D filtered back projection). In this way, the data is converted from projection space to image space, a domain that may be more understandable by a user 128 viewing the image(s), for example.

The example environment 100 also includes a terminal 132 (e.g., a computer) configured to receive the image(s), which can be displayed on a monitor 126 of the terminal 132 to a user 128 (e.g., security personnel, medical personnel, etc.). In this way, a user 128 can inspect the image(s) to identify areas of interest within the object(s) 104. The terminal 132 can also be configured to receive user input which can direct the object scanning apparatus 102 how to operate (e.g., a speed to rotate, a speed of a conveyor belt, etc.) and/or can direct the terminal 132 to display an image of the object(s) 104 from a particular angle, for example.

In the example environment 100, a controller 130 is operably coupled to the terminal 132 comprising the monitor 126. In one example, the controller 130 is configured to receive user input from the terminal 134 and generate instructions for the object scanning apparatus 102 indicative of operations to be performed. For example, the user 128 may want to rescan the object(s) 104, and the controller 130 may issue an instruction instructing the support article 110 to reverse direction (e.g., bringing the object(s) 104 back into an examination region 112 of the object scanning apparatus 102).

Figure 1B:
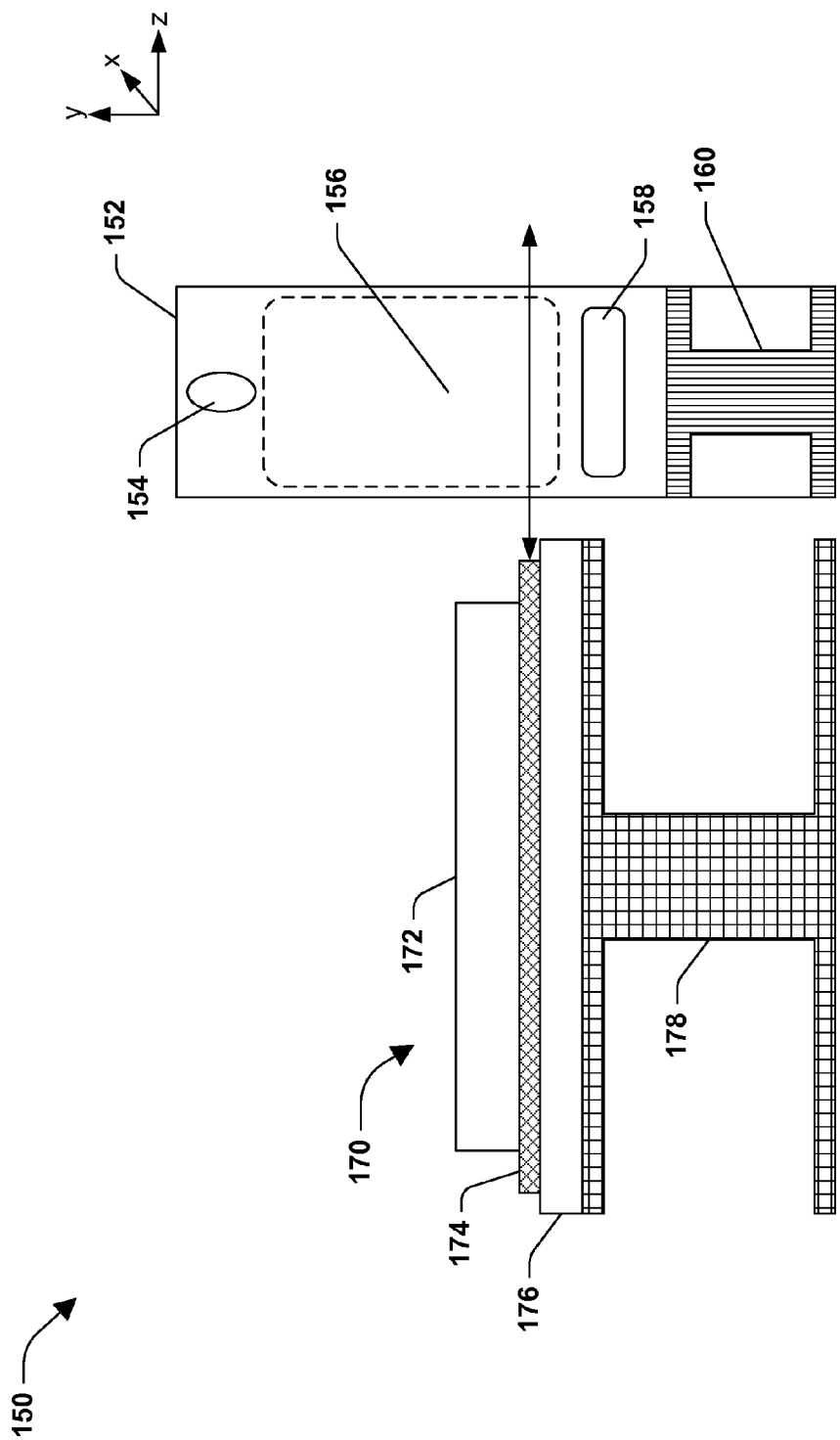
FIG. 1B is a component diagram illustrating an example embodiment of a conventional radiology system.

FIG. 1B is a component diagram illustrating an example embodiment 150 of a conventional radiographic scanning system. In this example embodiment 150, the radiographic scanning system comprises a radiographic apparatus 152 (e.g., CT scanner, PET scanner, etc.) and a table assembly 170. Further, in this embodiment 150, the radiographic apparatus 152 and table assembly 170 are completely separate components that are separately secured to a floor. For example, a radiographic apparatus support 160 can be secured to the floor of an examination room, and a table assembly support 178, which provides support and vertical adjustment for table assembly 170 and an object disposed thereon 172, can be aligned with the radiographic apparatus 152, and secured to the floor separately.

In this embodiment 150, the table assembly comprises a table surface 174, which can be used for holding the object 172 during a scanning operation, and a table surface mover 176, which allows and/or provides for moving the table surface 174 into and out of an examination region 156 of the radiographic apparatus 152. For example, prior to a scanning operation the object 172 (e.g., patient) is placed onto the table surface 174, which is integral to the table assembly 170. During the scanning operation, in this example, the table surface 174 and object 172 thereon can be moved (in a z direction) into the examination region 156 of the radiographic apparatus 152, while a radiation source 154 and a detector array 158, comprised in a rotating gantry (not shown), complete rotations (in an x, y plane) about the examination region.

Further, during the scanning operation, in this example, the table surface 174 is extended into the examination region 156 in a cantilevered fashion, while the table surface 174 remains operably attached to the table surface mover 176. Additionally, the table surface mover 176 is supported by the table support 178, which, in turn, provides support for the table surface 174 and object thereon 172. Upon completion of the scanning operation, for example, the table surface can be moved back out of the examination region 156, and the object 172 can be removed from the table surface 174, such as onto a waiting gurney to move the patient.

Figure 2:
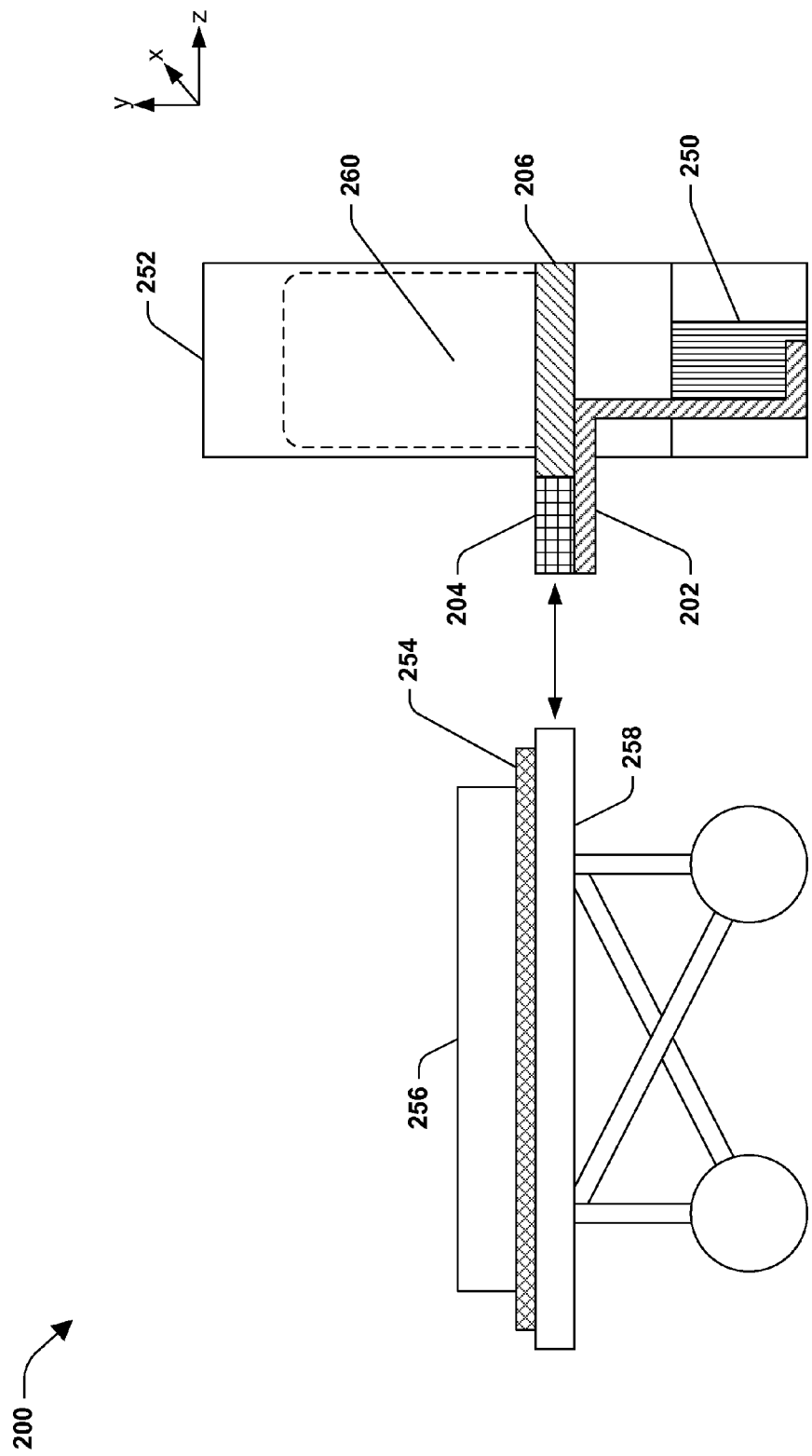
FIG. 2 is a component diagram illustrating one or more portions of an example apparatus for handling an examination surface.

FIG. 2 is a component diagram illustrating one or more portions of an example apparatus 200 for handling an examination surface (e.g., 110 of FIG. 1) for radiographic scanning or other operations. The example apparatus 200 comprises an examination surface support structure 202 that is integrally coupled with a support component 250 of a radiographic scanning apparatus 252. The examination surface support structure 202 provides support for an examination surface 254 and an object 256 that may be placed thereon, such as during a radiographic scanning operation (e.g., a CT scan).

For example, in previous and current radiographic systems, such as CT scanners, PET scanners, SPECT systems, MRI devices, radiation therapy devices and combination(s) thereof in a medical diagnostic or therapy setting, a patient table is a separate assembly from that of the scanner or radiation dosage device, providing its own support for an examination surface that is part of the table and for a patient on the examination surface. In contrast, in this embodiment 200, the support function 202 for the examination surface 254 during a scanning or therapy operation is provided by the apparatus support 250, for example, and comprised in the apparatus 200 instead of a separately attached table.

The example apparatus 200 further comprises an examination surface docking component 204 that is operably coupled with the examination surface support structure 202. The examination surface docking component 204 docks with an examination surface transport component 258 in order to exchange the examination surface 254 between the transport component 258 and the radiographic scanning apparatus 252. That is, for example, the examination surface docking component 204 can interface with the transport component 258 (e.g., a gurney) such that the examination surface 254 (e.g., back board) may be moved (e.g., slid) directly into/onto the docking component 204, and thus into the radiographic apparatus 252 (e.g., CT scanner). The docking component 204 can be supported by the examination surface support structure 202, for example, thereby providing support for the examination surface 254 (e.g., and optionally an object 256 thereon) when moved (e.g., in a z direction) to the docking component 204. It will be appreciated that as yet undocked portions of the examination surface 254 (e.g., an opposing end of the examination surface 254) may remain on/supported by the transport component 258 as the examination surface 254 is slid into the docking component 204 (in a z direction) such that the examination surface 254 may need to be less rigid (e.g., thick) than conventional surfaces which have to provide cantilevered support of the (e.g., often weighty) object 256. Accordingly, the (e.g., thinner) examination surface 254 may attenuate significantly less radiation than conventional surfaces, allowing similar image resolution to be obtained with a reduced radiation dose. That is, handling an examination surface as provided herein, in addition to being accurate, allows the examination or operational surface to be significantly more translucent with regard to radiation and/or photons, for example.

Additionally, in this way, for example, a patient (e.g., object 256) can be prepared for scanning in a separate area from a CT scanner or radiotherapy device (e.g., radiographic apparatus 252), such as in the patient's room, by placing them on the examination surface (e.g., 254), and placing the examination surface on a gurney (e.g., transport component 258). Further, in this example, the gurney, with the patient and examination surface disposed thereon, can be readily transported to the CT scanner. The patient can then be moved onto/into the scanner (in a z direction) without having to lift the patient from the gurney to a scanner bed, in this example, by moving the examination surface 254 with the patient situated thereon into/onto a dock of the CT scanner (e.g., docking component 204). The patient can them be examined by a gantry that rotates around the patient in an x, y plane, for example.

Additionally, the example apparatus 200 comprises an examination surface transit component 206 that is operably coupled with the examination surface support structure 202. The examination surface transit component 206 moves the examination surface 254, and the object 256 optionally placed thereon, into and out of an examination or operation region 260 (e.g., examination or dosage region) of the radiology or radiotherapy apparatus 252. That is, for example, the transit component 206 can be supported by examination surface support structure 202, which can be integrated with the radiographic apparatus's support component 250, in order to provide support for the examination surface 254, and object 256 thereon, while it is moved into and out of the examination region 260 during a scan.

Figure 3:
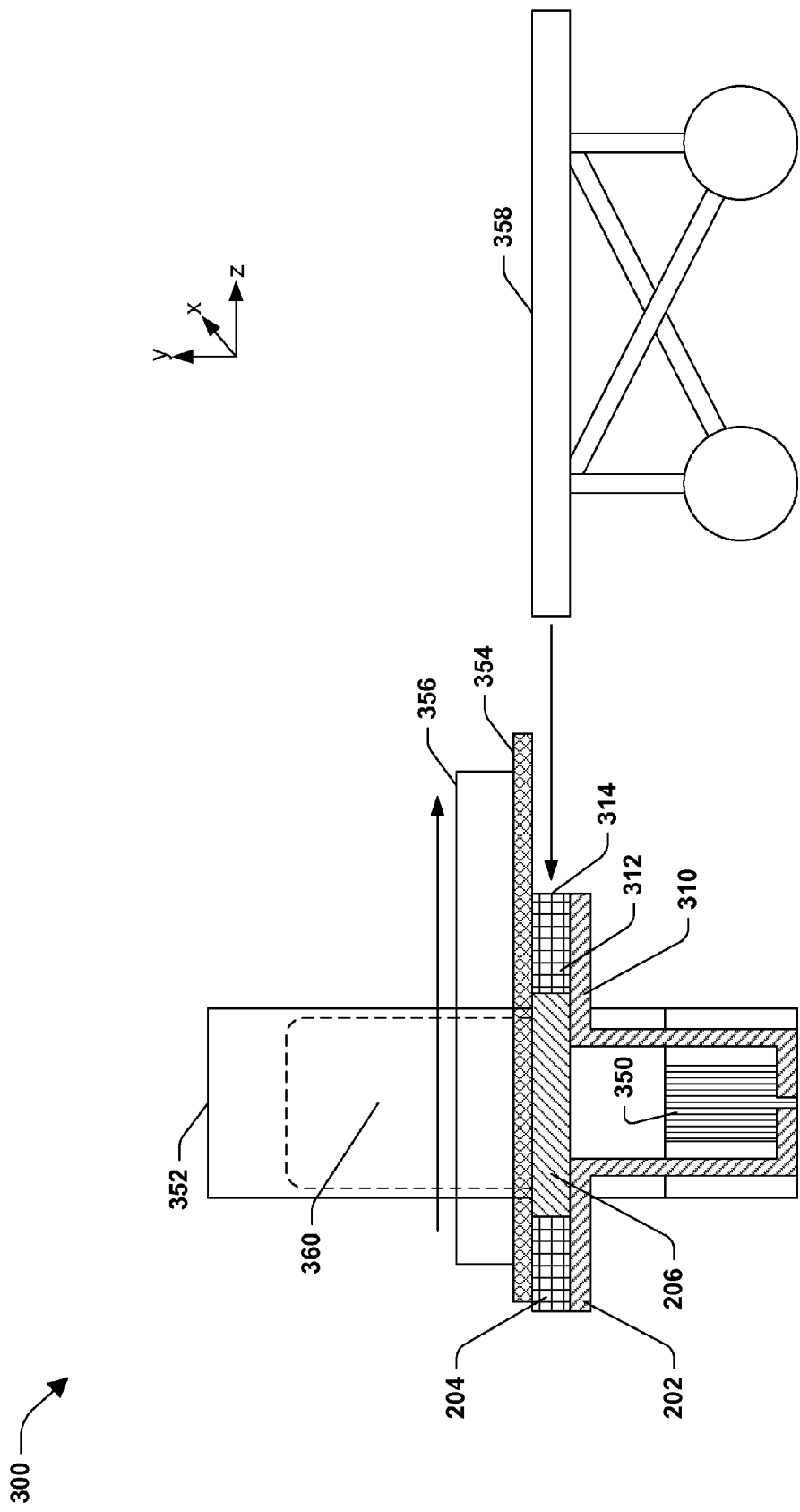
FIG. 3 is a component diagram illustrating an example embodiment of one or portions of an apparatus described herein.

FIG. 3 is a component diagram illustrating an example embodiment 300 of one or more portions of an apparatus utilizing one or more systems described herein. In the example embodiment 300, a radiographic apparatus can comprise a first examination surface docking component 204 that is disposed on a first side of the radiographic scanning apparatus 352, and a second examination surface docking component 312 that is disposed on a second side of the radiographic scanning apparatus 352. Further, in this embodiment, the second examination surface docking component 312 can be operably coupled with a second examination surface support structure 310, which may be integrated with the support component 350 for the scanning apparatus 352, for example, and which may also be integral with a first examination surface support structure 202.

In one embodiment, the examination surface 354, with an object 356 (e.g., patient) optionally disposed thereon, may be exchanged from a transport component 358 (e.g., or optionally a different transport component, such as 256 of FIG. 2) to the first examination surface docking component 204 on a first side of the radiographic scanning apparatus 352. As an example, the object 356 can be subjected to a scanning operation (e.g., CT scan), such as by moving the examination surface 354 and object 356 through an examination region 360 of the radiographic apparatus 352 using the transit component 206.

In this embodiment, the transport component 358 (e.g., gurney) can be docked with (interface with) a dock face 314 of the second examination surface docking component 312 on the second side of the radiographic scanning apparatus 352, such as after the scanning operation is completed. In this way, for example, the examination surface 354, and object 356 thereon, can be fed into the radiographic apparatus 352 from a transport component (e.g., 258 or 358) via the first docking component 204 and transit component 206, and conveyed through and out of the radiographic apparatus 352 onto a transport component (e.g., 258 or 358) via the second docking component 312 and transit component 206. Accordingly, in this example, a patient may be moved to and from a scanning apparatus, and have a scanning operation performed, without having to be moved from the examination surface 354 because the examination surface is selectively received by support structure(s) of the scanning system. It will be appreciated that the examination surface docking component (e.g., 204 of FIG. 2, 312 of FIG. 3) can comprise at least one channel that has an opening (e.g., "c" shaped in cross-section) disposed at a docking face (e.g., 314 of FIG. 3). In one embodiment, the channel can provide guidance for the examination surface (e.g., 254 of FIG. 2, 354 of FIG. 3) to interface with the examination surface transit component 206. Further, in one embodiment, the channel can, for example, provide support for the examination surface (e.g., 254 of FIG. 2, 354 of FIG. 3) while extended beyond a face of the examination surface docking component (e.g., 204 of FIG. 2, 312 of FIG. 3).

Figure 4A:
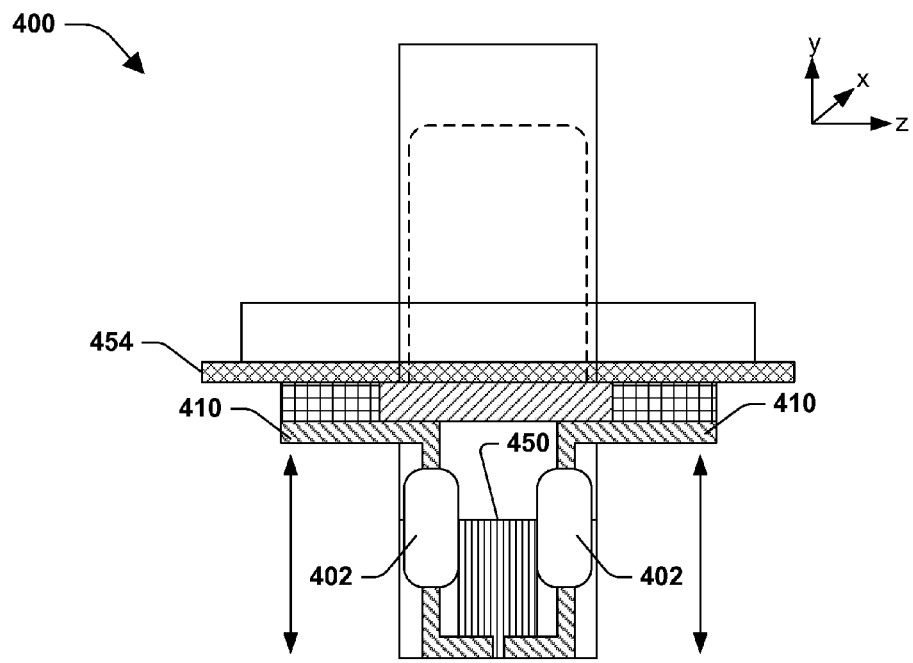
FIGS. 4A and 4B are component diagrams illustrating example embodiments of one or more portions of an apparatus described herein.
Figure 4B:
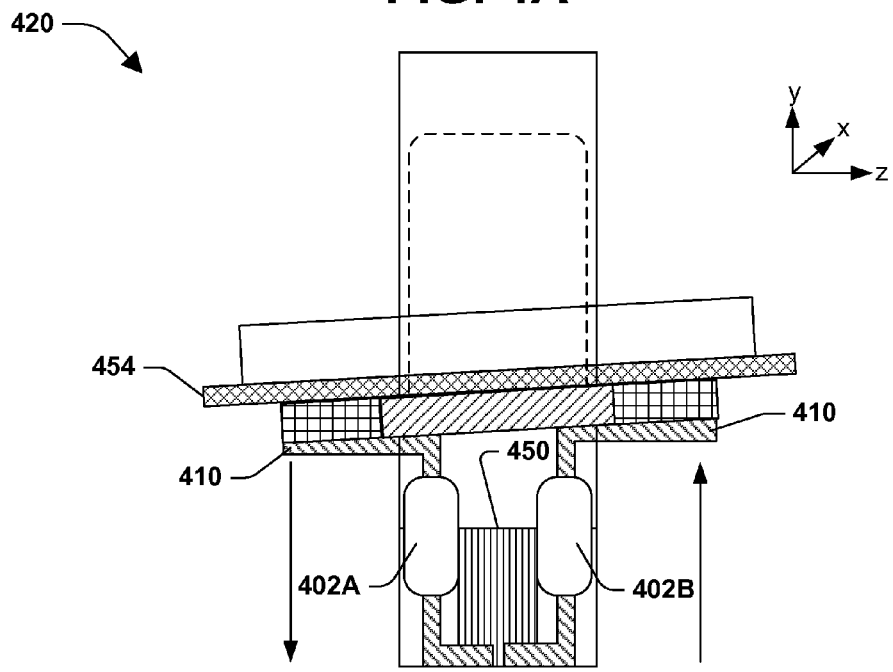

FIGS. 4A and 4B are example embodiments 400, 420 illustrating one or more portions of an apparatus comprising one or more systems or aspects described herein. In FIG. 4A, the example embodiment of a radiographic apparatus 400 comprises a height adjustment component 402 that is integrally coupled with an examination surface support structure 410, which is integrally coupled with a radiographic apparatus support component 450. On or more height adjustment components 402 can be used to raise and lower the examination surface 454. For example, the one or more height adjustment components 402 can be used to place an object in a desired position in an examination region of the radiographic apparatus (e.g., to provide focus for the scanning operation).

In one embodiment, the height adjustment component(s) 402 can comprise at least two lifters that are respectively disposed at a first and second side of the examination surface support structure 410. That is, as shown in the example embodiment 400 of FIGS. 4A and 420 of FIG. 4B, respective lifters 402 can be integrally coupled with separate support components 410, such that respective lifters 402 can independently affect the height of the examination surface 454. In this embodiment, the at least two lifters 402 can concurrently raise and concurrently lower the examination surface, as illustrated in FIG. 4A.

Further, in one embodiment, the at least two lifters 402A and 402B can independently raise and independently lower the examination surface 454, as illustrated in FIG. 2B. For example, lifter 402A may be lowered while lifter 402B can be raised. In this way, in this example, the examination surface 454 (e.g., and an object thereon) can be optionally tilted, such as to provide an alternate image slice of an object, and/or to provide for a desired positioning of the object within the examination region during a scanning operation.

Figure 5A:
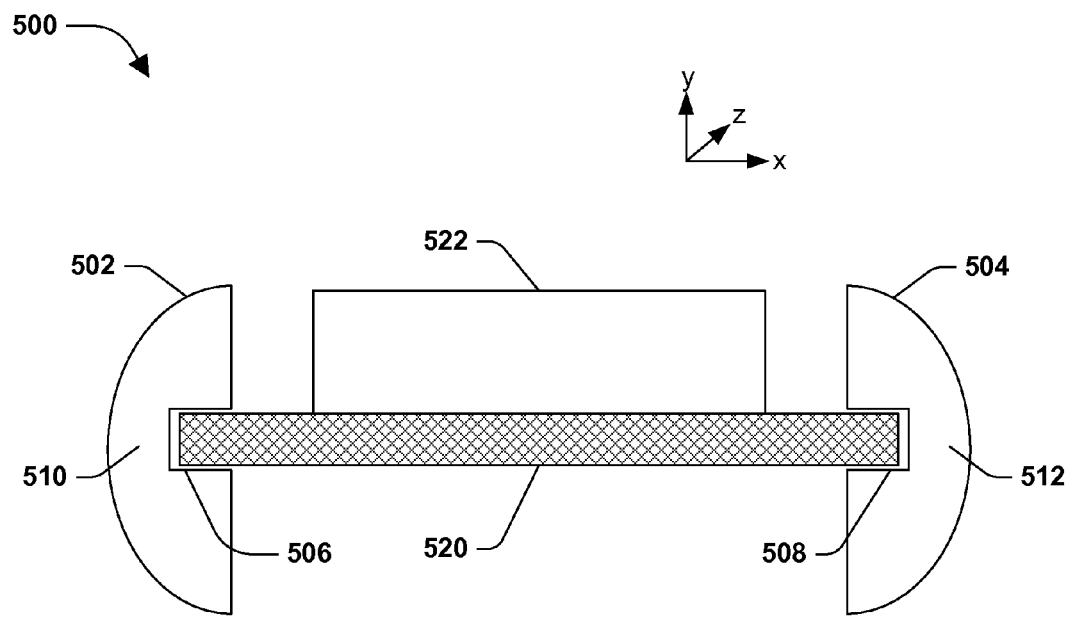
FIGS. 5A and 5B are component diagrams illustrating example embodiments of one or more portions of an apparatus described herein.
Figure 5B:
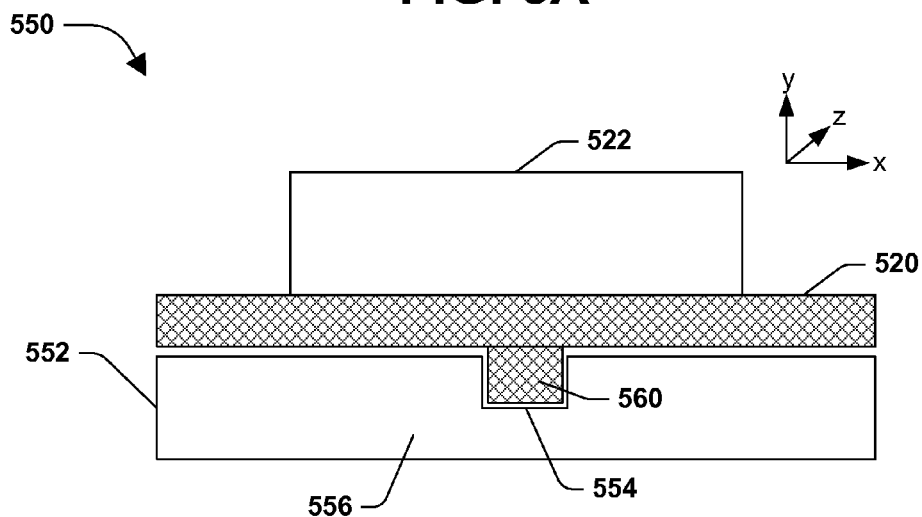

FIGS. 5A and 5B are component diagrams illustrating example embodiments 500 and 550 of one or more components of an apparatus described herein. In the example embodiment 500 of FIG. 5A, a first examination surface docking component 502 comprises a first channel 506, which is open to a first docking face 510 of the first examination surface docking component 502. Further, in this example embodiment 500, a second examination surface docking component 504 comprises a second channel 508, which is open to a second docking face 512 of the second examination surface docking component 504. In this way, for example, an examination surface 520 (e.g., and an object 522 optionally disposed thereon 522) can interface with the one or more docking components 502, 504 at their docking faces 510, 512 by engaging with the channels 506, 508 of the respective examination surface docking components 502, 504. In this example, this engagement may allow the examination surface 520 (and associated object 522) to slide into and out of a radiographic scanning system in a z direction into and out of the page.

In FIG. 5B, an alternate embodiment 550 comprises a single channel 554 disposed in the examination surface docking component 552. In this embodiment, the channel 554 is open to the docking face 556 of the examination surface docking component 552, such that the examination surface 520 can interface with the examination surface docking component 552 by engaging a portion 560 of the examination surface 520 with the channel 554. In the example embodiments 500 and 550, the one or more channels 506, 508, 554 can guide the examination surface 520 to a transit component (not shown), for example, where the transit component is disposed at an opposite end from the docking face 510, 512, 556. Further, the one or more channels 506, 508, 554, and more particularly the examination surface docking components 510, 512, 552, can provide support for the examination surface 520, such as during an exchanging of the examination surface 520 to or from a transport component (not shown) (e.g., gurney), as the examination surface docking components 510, 512, 552 comprising the channels 506, 508, 554 can be operably coupled with an examination surface support structure (e.g., 202, 310 of FIG. 3).

It will be appreciated that the examination surface docking components 510, 512, 552, and channels 506, 508, 554, disposed therein, is not limited to a particular length or configuration. For example, an examination surface docking component may comprise a channel that is merely sufficient to receive the examination surface and guide it to a transit component. As another example, the examination surface docking component may comprise a channel that has sufficient length to provide support for the examination surface if it is extended beyond the docking face, and not supported by the transport component. As a further example, the channel may comprise sufficient width such that a portion of the examination surface is encompassed by the channel (e.g., as illustrated in FIG. 5A), thereby providing a support for the examination surface when extended.

In one embodiment, the examination surface transit component may comprise a plurality of rollers that are arranged to facilitate moving the examination surface into and out of an examination region. As an illustrative example, FIG. 6A is example embodiment 600 of one or more portions of an apparatus described herein. In this example embodiment 600, a set of rollers 602 can be provided in an array to allow the examination surface 650 and an object thereon 652 to be moved into and out of the examination region (not shown), such as during a scanning operation (e.g., in a z direction into and out of the page).

FIGS. 8 and 9 provide other illustrative examples 800 and 900 of an arrangement of rollers that may be employed by the transit component. In the example 800 rollers 808 are arranged such that the examination surface 804 can be moved into the examination region 810 of the radiographic apparatus 802. In the example 900, the rollers 808 may be arranged in a linear manner (e.g., in the 'z' direction) such that the examination surface 804 can be moved into and out of the examination region. In these examples 600, 800, 900, the rollers are aligned in a manner that can facilitate keeping the examination surface aligned in the 'x' direction, for example, by arranging them at an angle that meets an angled component of (the bottom of) the examination surface.

In another embodiment, the examination surface transit component can comprise a drive component that interfaces with at least a portion of the examination surface, and automatically moves the examination surface into and out of the examination region. In one embodiment, the drive component can comprise mechanically operated rollers that interface with a drive interface component on the examination surface. As an illustrative example, in FIG. 6A, the rollers 602 may be mechanically operated (e.g., driven by a motor directly or indirectly—not shown), and they can interface with the drive interface component 606 (e.g., angled component) of the (bottom of the) examination surface 650.

In one embodiment, the drive interface component 606 may comprise a traction component, such as grooves, ridges, a gripping surface, or some means of providing traction for the (bottom of the) examination surface 650 on the rollers 602. Further, in this example, the interface for the drive component may also comprise a guidance component 604 (e.g., comprising channel 554 of FIG. 5B) that can guide the examination surface along the z direction while keeping it aligned in the x direction. For example, when performing a scanning operation, such as in a CT scanner, the object subjected to the scan may need to be in a particular position in the examination region in order to provide for desired focus for imaging the object. In this example, the guidance component 604 can provide, or rather maintain, appropriate alignment in the x direction when moving the examination surface in the z direction into the examination region. It will be appreciated that bevels 606 of the examination surface 650, and their respective relationships with rollers 602, may serve this purpose as well, alone or in conjunction with a guidance component. It can thus be appreciated that one or more of the techniques and/or systems provided herein provide for accurate handling of an examination or operational surface.

In another embodiment, the drive component can comprise a mechanically operated track component having one or more examination surface interface components that interface with one or more drive interface components on the (bottom of the) examination surface. As an example, in FIG. 6B, the example embodiment 630 illustrates a mechanically operated track component 638, such as a flexible belt or chain, which has examination surface interface components 634 that can interface with drive interface components 632 on the examination surface 650. For example, the track component 638 may comprise a polymer belt having ridges 634 that are aligned with spaces between teeth 632 on the underside of the examination surface 650. In this way, in this example, gears or rotors 636 may be mechanically operated (e.g., driven directly or indirectly by motors—not shown) to move the examination surface 650 in the z direction 654 with an accuracy appropriate for the operation.

In one embodiment, the drive component can comprise one or more electro-magnet components that provide electromagnetic propulsion for the examination surface. As an example, in FIG. 6C, the example embodiment 660 illustrates an arrangement where electro-magnetic propulsion may be employed. An electromagnet can comprise an array of metallic plates 668 aligned vertically along the z direction, for example, that are magnetically charged by a polarizing component 664. The electromagnet can interface with an electro-magnetic interface component 670 on the examination surface, for example, whereby magnetic pulses are moved along the array of metallic plates 668 to move the examination surface along the z direction. In one embodiment, rollers 662 may be used to provide stability, proper alignment, and/or facilitate moving the examination surface 650.

As an illustrative example, in FIGS. 8 and 9, a drive component 806 is illustrated as comprising, among other things, rollers 808. The drive component 806 may interface with the examination surface 804 at a point proximate to the examination region 810 in order to automatically move the examination surface through the examination region 810 at a desired speed in accordance with a scanning operation, for example. That is, the transit component may utilize rollers, for example, to move (either manually or mechanically) the examination surface from the docking component (not shown) to the drive component 806, whereupon the drive component 806 can move the examination surface 804 through the examination region 810.

FIG. 7 is a component diagram illustrating an example embodiment 700 of one or more components of an apparatus described herein. In this embodiment 700, a docking extension component 730 is operably coupled with an examination surface docking component 704. In this embodiment, the docking extension component 730 can provide an extended docking location, such as for docking with a transport component 758 (e.g., a gurney). Further, the docking extension component 730 can provide support for the examination surface 754 and an object 756 optionally placed thereon when docked on the docking extension component 730.

In one embodiment, a first docking extension component 730A can be coupled to a first docking component 704A at a first side of the radiographic apparatus 752; and a second docking extension component 730B can be coupled to a second docking component 704B at a second side of the radiographic apparatus 752. As an illustrative example, a first examination surface 754A, with first object 756A thereon, can be exchanged from a first transport component (not shown) to the first docking extension component 730A. In this example, relatively concurrently, a (previously scanned) second examination surface 754B, with second object 756B thereon, can be exchanged from a second docking extension component 730B to a second transport component 758. It will be appreciated that a transit component and/or other components, such as described herein, may be implemented to effect such movement (in the z direction).

In this way, for example, the first examination surface 754A can be moved into the examination region 760 for a scan, while the (just scanned) second examination surface 754B is removed. As another illustrative example, in FIG. 9, a plurality of examination surfaces 804A, 804B, 804C may be used. In this example, a first examination surface 804A is loaded, while a second examination surface may be used in a scanning operation in the examination region 810, and a third examination surface 804C is unloaded. In this way, for example, a plurality of objects, such as patients, can be sequentially scanned in a manner that provides greater efficiency, which may be advantageous in densely populated areas having few radiographic scanning systems, for example. Likewise a patent on a backboard, for example, could be directly moved from an ambulance, for example, through a radiographic scanning system, possibly through a receiving bore or hole in an external wall of a medical facility. That is, the ambulance could be backed up to the facility and the patient could be conveyed directly through the scanning system. Moreover, again, since the examination surface may merely comprise a relatively thin (poly, plastic, wood, etc.) surface, the scan may be performed with a reduced radiation dose.

A method may be devised that provides for a more efficient way to scan objects, such as for a radiology operation by providing accurate integration of an examination surface with a device used for scanning or dosage. FIG. 10 is a flow diagram of an example method 1000 for handling an examination surface having an object optionally situated thereon for examination with an apparatus, such as a radiographic apparatus, for example. The example method 1000 begins at 1002 and involves interfacing a transport that is carrying the examination surface, having an object optionally placed thereon, with an examination surface dock (or docking component) on the apparatus, at 1004. For example, the transport may comprise a gurney that is transporting a patient on the examination surface. In this example, the gurney can be docked with (e.g., aligned against) the examination surface dock.

In one embodiment, the examination surface dock may be designed to align with the transport component, for example, where the transport component, and/or the examination surface dock can be raised or lowered (e.g., via lifters) to accommodate a desired docking interface (e.g., alignment), such that the examination surface may be appropriately exchanged. At 1006, the examination surface is exchanged between the transport and the examination surface dock. For example, the examination surface dock can be aligned (docked) with the transport component in a way that allows for the examination surface to be moved from the transport to the examination surface dock.

In one embodiment, examination surface dock can be supported by a support structure that is integrated with a support component of the apparatus, in order to support the examination surface and the object optionally placed thereon, during the exchanging. Further, for example, the examination surface may be exchanged from the examination surface dock to the transport, such as after a scanning operation is completed. As an example, after a patient's CT scan is completed, they can be remain on the examination surface and be moved back to the gurney using the examination surface dock, which is aligned with the gurney.

In one embodiment, exchanging the examination surface between the transport and the examination surface dock can be performed at a same side of the apparatus. In another embodiment, the examination surface can be exchanged in at a first side of the apparatus (e.g., loaded onto the radiographic apparatus), and exchanged out at a second side of the radiographic apparatus (e.g., loaded back onto the transport).

At 1008, the examination surface is engaged with an examination surface transit so that the examination surface can be moved into and out of an examination region of the apparatus with, for example, the appropriate levels of stability and accuracy. In one embodiment, the examination surface transit can be used to automatically move the examination surface into and out of the examination region (along a z direction for scanning). For example, a portion of the examination surface may engage with a mechanically driven portion of the transit that provides for moving the examination surface, such as may be controlled by an operator and/or programmatically. The mechanically driven portion of the transit component may comprise a series of rollers (e.g., either free rolling and/or mechanically driven), a track (e.g., flexible belt or chain) that is mechanically driven, some electromagnetic propulsion drive, and/or a combination of these and/or other drive means, for example.

As described above, engaging with the transit component allows for the examination surface and object, for example, to be moved through the examination region for an operation. Further, once engaged with the transit component, the examination surface can be move out of the examination region, such as after scanning or dosage is completed, and to the docking component, where the examination surface can then be exchanged to the transport component. Additionally, in one embodiment, the transit can be supported by a support structure that is integrated with the support component of the apparatus, so that the examination surface and the object thereon are supported during the operation. That is, given that the support structure is integral with the support component of the apparatus, the transit is effectively supported by the same (composite) structure that is supporting the apparatus.

Having engaged the examination surface with the examination surface transit, to move the examination surface into and out of the examination region, the example method 1000 ends at 1010.

FIG. 11 is a flow diagram of an example embodiment 1100 of one or more portions of a method described herein. At 1102, a target object (e.g., patient) is transported on an examination surface using a transport. For example, a patient may be prepared for a scan in a first location (e.g., patient room, triage, scan prep area) and moved to a scanning apparatus in a second location. In this example, the patient can be placed on the examination surface, such as at an emergency location, and the examination surface can be interfaced with the transport. In this way, for example, the examination surface may be a modular component that can stay with the patient, and interfaced with a plurality of other components to move the patient (e.g., from an emergency, to an ambulance, to a gurney, to a CT scanner).

At 1104, the transport is interfaced with a dock of the radiology or radiotherapy apparatus. For example, the transport comprising the examination surface can be docked with a docking face of the dock, such that the examination surface is aligned with the dock in preparation for exchanging the examination surface. At 1106, the examination surface is exchanged between the transport and the examination surface dock by interfacing at least a portion of the examination surface with at least one channel through an opening in the face of the examination surface dock. For example, the docking face may comprise a channel that part of the examination surface can slide into, thereby engaging the examination surface with the dock.

At 1106, once engaged, the examination surface can be exchanged from the transport to the dock. For example, the dock can provide support for the examination surface, such as by one or more channels encircling portions (e.g., side edges) of the examination surface. Once the examination surface is exchanged with the dock from the transport, for example, the support can be provided by the docking component, and/or in combination with the transport until the transport is moved away from the dock. The dock can be supported by a support structure that is integrated with the apparatus support, for example, thereby allowing the examination surface to extend beyond the docking face without the transport providing support.

At 1110, a portion of the examination surface is engaged with the examination surface transit. For example, as illustrated in FIG. 9, an angular portion of the examination surface 804A is engaged with rollers 808 of the transit. In this way, the examination surface can be moved in a z direction, for example. As another example, a drive interface portion (e.g., ridges, indentations, gear lines, etc.) of the examination surface may be engaged with a drive portion (e.g., wheels, track, electromagnet) of the transit, in order to automatically or programmatically move the examination surface in the z direction.

At 1112 of the example embodiment 1100, the examination surface is moved into the examination area (e.g., where scanning or dosage can occur) of the apparatus, using the examination surface transit. In one embodiment, the examination surface may be manually moved into the examination region, where it can be temporarily engaged with a mechanically driven transit component that automatically moves the examination surface during the scan (e.g., programmatically or commanded by a controller/technician). In another embodiment, the examination surface may be engaged with the mechanically driven transit component at or near the dock, where it can move the examination surface automatically during an entire operation (e.g., moving patient with transit, into examination region, out of examination region to second dock).

In one embodiment, at 1114, while a first examination surface is engaged by the examination surface transit, a second examination surface can be exchanged between the transport and the examination surface dock. That is, for example, a second patient may be transported to the CT scanner, at 1102, interfaced with the dock, at 1104, and exchanged to the dock, at 106, while the first patient is undergoing a scanning operation. A an illustrative example, in FIG. 9, an object on a first examination surface 804C may have completed its operation and is being removed by a first transport, while an object on a second examination surface 804B is undergoing a scan, while an object on a third examination surface 804A is being exchanged with the dock from a second transport in preparation for a scan.

At 1116, in preparation for the operation, a height and/or angle of the examination surface can be adjusted using one or more lifters coupled with the support structure, which is further integrated with the support component of the radiographic apparatus. That is, for example, a first lifter may be attached to a first support structure on a first side of the examination region, and a second lifter can be attached to a second support structure on a second side of the examination region (e.g., opposite side in the z direction). In this way, in this example, the examination surface can be raised or lowered to provide desired focal points for the scan, by concurrently raising or lowering the two lifters. Alternately, in this example, the lifters can be raised or lowered independently to adjust the angle of the examination surface. In one embodiment, such adjustments in height and/or angle can also be accomplished by inserting radio translucent pads of the appropriate thickness and shape between the operating surface and the patient.

At 1118, the object is subjected to the operation, and the examination surface is moved out of the examination region using the transit, at 1120. At 1122, the transport (e.g., or another transport) is interfaced with the second dock at the second side of the radiographic apparatus, and the examination surface is exchanged from the second dock to the transport. At this time, the examination surface, and object thereon, can be moved to another location (e.g., back to the patient room, surgery, recovery, etc.) using the transport (e.g., gurney).

In an alternate embodiment, with reference to FIGS. 1A and 2, a radiology system, such as illustrated in 100 of FIG. 1, can comprise a rotating gantry portion 106 and a non-rotating portion 108 that is associated with the rotating portion 106 in order to facilitate examination of an object 104. In this alternate embodiment, a support structure, such as 202 of FIG. 2, is associated with the non-rotating portion 108 (e.g., the structural component of the non-rotating portion 250). The support structure 202 can selectively receive one or more examination surfaces 254, 110 such that one or more objects 256, 104 optionally placed upon respective examination surfaces 254, 110 may be examined. Further, in this alternate embodiment, the support structure 202 can articulate the examination surface 254, and an object thereon 256, relative to the non-rotating portion 108.

By way of further example, a docking component (such as 204 of FIG. 2) may be operably coupled with the support structure 202. In this embodiment, the docking component 204 can dock (e.g., align, interface) with an examination surface transport component, such as 258 of FIG. 2, in order to exchange the examination surface 254 between the transport component 258 and the support structure 202.

In another embodiment, with reference to FIGS. 2 and 7, the support structure 202 can concurrently accommodate at least a portion of a first examination surface 754B and at least a portion of a second examination surface 754A as the first examination surface 754B is articulated out of the scanning system 752 and the second examination surface 754A is articulated into the scanning system 752. That is, for example, the radiographic scanning system in this alternate embodiment can accommodate a plurality of examination surfaces, such as illustrated in FIG. 9, where a semi-continuous scanning operation may be accomplished by continually moving examination surfaces into and out of the radiographic scanning system while scans are being performed.

It will be appreciated that the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An apparatus for handling a first examination surface configured to support a first object and a second examination surface configured to support a second object, comprising:
   an examination surface support structure configured to provide support for the first examination surface and the second examination surface;
   an examination surface transit component operably coupled with the examination surface support structure and configured to move the first examination surface relative to an operation region of the apparatus; and
   an examination surface docking component operably coupled with the examination surface support structure and configured to dock with an examination surface transport component to exchange the second examination surface between the examination surface transport component and the apparatus while the examination surface transit component is moving the first examination surface relative to the operation region.

2. The apparatus of claim 1, comprising a height adjustment component operably coupled with the examination surface support structure and configured to selectively tilt at least one of the first examination surface or the second examination surface.

3. The apparatus of claim 1, comprising a height adjustment component comprising a first lifter and a second lifter, the first lifter disposed on a first side of the operation region and the second lifter disposed on a second side of the operation region.

4. The apparatus of claim 1, the examination surface docking component disposed on a first side of the apparatus and a second examination surface docking component disposed on a second side of the apparatus.

5. The apparatus of claim 1, the examination surface transit component comprising a drive component configured to move at least one of the first examination surface or the second examination surface relative to the operation region.

6. The apparatus of claim 5, the drive component comprising a mechanically operated roller.

7. The apparatus of claim 5, the drive component comprising a mechanically operated track.

8. The apparatus of claim 5, the drive component comprising an electro-magnetic component.

9. The apparatus of claim 1, the examination surface support structure comprising a first roller configured to rotate about a first axis of rotation and contact a first beveled edge of the first examination surface.

10. The apparatus of claim 9, the examination surface support structure comprising and a second roller configured to rotate about a second axis of rotation and contact a second beveled edge of the first examination surface.

11. The apparatus of claim 10, the first axis of rotation not parallel to the second axis of rotation.

12. A method for handling an examination surface configured to support an object undergoing an operation via an apparatus, comprising:
    interfacing an examination surface transport component carrying the examination surface with an examination surface docking component;
    exchanging the examination surface between the examination surface transport component and the examination surface docking component;
    engaging the examination surface with an examination surface transit component configured to move the examination surface relative to an operation region of the apparatus; and
    exchanging the examination surface between a second examination surface transport component and at least one of:
        a second examination surface docking component, or
        the examination surface docking component.

13. The method of claim 12, comprising adjusting a height of the examination surface relative to the operation region.

14. The method of claim 12, comprising adjusting an angle of the examination surface relative to the operation region.

15. The method of claim 12, the exchanging the examination surface between the examination surface transport component and the examination surface docking component comprising docking the examination surface into a channel formed by the examination surface docking component.

16. The method of claim 12, comprising exchanging a second examination surface between a third examination surface transport component and the examination surface docking component while the examination surface is within the operation region.

17. The method of claim 12, the examination surface transport component and the second examination surface transport component being a same transport component.

18. A radiation system, comprising:
    a rotating gantry portion;
    a non-rotating portion operably associated with the rotating gantry portion to facilitate an examination of an object;
    an examination surface support structure operably coupled with the non-rotating portion and configured to move at least a first examination surface configured to support a first object and a second examination surface configured to support a second object through the rotating gantry portion, the examination surface support structure configured to concurrently accommodate the first examination surface and the second examination surface; and
    an examination surface docking component operably coupled with the examination surface support structure and configured to dock with an examination surface transport component to exchange the first examination surface between the examination surface support structure and the examination surface transport component.

19. A method for handling an examination surface configured to support an object undergoing an operation via an apparatus, comprising:
    interfacing an examination surface transport component carrying the examination surface with an examination surface docking component;
    exchanging the examination surface between the examination surface transport component and the examination surface docking component;
    engaging the examination surface with an examination surface transit component configured to move the examination surface relative to an operation region of the apparatus; and
    exchanging the examination surface between a second examination surface transport component and the examination surface docking component.

20. A method for handling an examination surface configured to support an object undergoing an operation via an apparatus, comprising:
    interfacing an examination surface transport component carrying the examination surface with an examination surface docking component;
    exchanging the examination surface between the examination surface transport component and the examination surface docking component;
    engaging the examination surface with an examination surface transit component configured to move the examination surface relative to an operation region of the apparatus; and
    exchanging the examination surface between a second examination surface transport component and a second examination surface docking component.

* * * * *